United States Patent
Mialhe

(10) Patent No.: US 10,925,635 B2
(45) Date of Patent: Feb. 23, 2021

(54) GUIDING APPARATUS AND METHOD FOR USE OF SAME

(71) Applicant: Claude Mialhe, Draguignan (FR)

(72) Inventor: Claude Mialhe, Draguignan (FR)

(*) Notice: Subject to any disclaimer, the term of this patent is extended or adjusted under 35 U.S.C. 154(b) by 265 days.

(21) Appl. No.: 15/902,630

(22) Filed: Feb. 22, 2018

(65) Prior Publication Data

US 2018/0177524 A1     Jun. 28, 2018

Related U.S. Application Data

(63) Continuation of application No. 12/304,882, filed as application No. PCT/EP2007/055615 on Jun. 7, 2007, now abandoned.

(30) Foreign Application Priority Data

Jun. 13, 2006 (FR) ...................................... 0652112

(51) Int. Cl.
| | | |
|---|---|---|
| *A61M 5/178* | (2006.01) | |
| *A61B 17/34* | (2006.01) | |
| *A61M 39/06* | (2006.01) | |

(52) U.S. Cl.
CPC ...... *A61B 17/3421* (2013.01); *A61B 17/3462* (2013.01); *A61B 17/3498* (2013.01);
(Continued)

(58) Field of Classification Search
CPC ............ A61B 17/3462; A61B 17/3498; A61B 2017/3445; A61B 2017/3466; A61M 2039/0626; A61M 39/06; A61M 39/0693
See application file for complete search history.

(56) References Cited

U.S. PATENT DOCUMENTS

| 4,538,594 A | 9/1985 | Boebel et al. |
| 4,540,411 A | 9/1985 | Bodicky |
| (Continued) | | |

FOREIGN PATENT DOCUMENTS

| EP | 0 834 279 | 4/1998 |
| WO | WO 00/32263 | 6/2000 |
| WO | WO 00/74760 | 11/2000 |

OTHER PUBLICATIONS

International Search Report dated Nov. 16, 2007, from corresponding PCT application.

*Primary Examiner* — Rebecca E Eisenberg
(74) *Attorney, Agent, or Firm* — The Farrell Law Firm, P.C.

(57) ABSTRACT

Provided is a method performing vascular surgery utilizing a guiding apparatus that includes an adaptor and an introducer, by inserting a longitudinal section of the adaptor into the introducer and operating a valve of the introducer by moving a cursor provided on a side wall of the introducer within a travel region of the cursor. Operating the valve either fixedly attaches or releases the longitudinal section of the adaptor within or from the introducer. The adaptor includes an inner volume that encloses a plurality of ducts and the introducer includes an inner volume that aligns with the inner volume of the adaptor when the valve is fixedly attached the longitudinal section of the adaptor within the introducer, thereby providing ducts that allow an instrument to pass entirely through both the adaptor and the introducer.

14 Claims, 11 Drawing Sheets

Related U.S. Application Data

(60) Provisional application No. 60/854,090, filed on Oct. 25, 2006.

(52) U.S. Cl.
CPC ........ *A61M 39/06* (2013.01); *A61M 39/0693* (2013.01); *A61B 2017/3445* (2013.01); *A61B 2017/3449* (2013.01); *A61B 2017/3466* (2013.01); *A61M 2039/0626* (2013.01)

(56) References Cited

U.S. PATENT DOCUMENTS

| | | | |
|---|---|---|---|
| 4,730,616 A * | 3/1988 | Frisbie | A61M 25/01 604/164.02 |
| 4,737,142 A | 4/1988 | Heckele | |
| 4,756,303 A | 7/1988 | Kawashima et al. | |
| 4,857,062 A | 8/1989 | Russell | |
| 5,106,368 A | 4/1992 | Uldall et al. | |
| 5,158,553 A | 10/1992 | Berry et al. | |
| 5,199,948 A | 4/1993 | McPhee | |
| 5,261,889 A | 11/1993 | Laine et al. | |
| 5,334,164 A * | 8/1994 | Guy | A61B 17/3462 604/246 |
| 5,603,702 A | 2/1997 | Smith et al. | |
| 5,749,889 A | 5/1998 | Baclch et al. | |
| 5,772,628 A | 6/1998 | Baclch et al. | |
| 6,234,958 B1 | 5/2001 | Snoke et al. | |
| 6,450,550 B1 | 9/2002 | Cornwell | |
| 7,387,624 B2 | 6/2008 | Nelson | |
| 7,753,901 B2 | 7/2010 | Piskun et al. | |
| 8,147,457 B2 | 4/2012 | Michael et al. | |
| 2002/0111585 A1 | 8/2002 | Lafontaine | |
| 2008/0009834 A1 | 1/2008 | Mialhe | |

\* cited by examiner

GUIDING APPARATUS AND METHOD FOR USE OF SAME

PRIORITY

This application is a Continuation of U.S. patent application Ser. No. 12/304,882 filed Dec. 15, 2008 as a National Phase Entry of International Application No. PCT/EP2007/055615 filed Jun. 7, 2007 and claims priority to French Application No. 0652112 filed Jun. 13, 2006 and to U.S. Provisional Patent Application No. 60/854,090 filed Oct. 25, 2006, the disclosure of each of which is incorporated herein by reference.

BACKGROUND OF THE INVENTION

1. Field of the Invention

The present invention generally relates to a valve introducer fitted with an adaptor for introduction into a human or animal body, particularly during vascular surgery.

2. Description of the Related Art

The instruments introduced into a human or animal body require the presence of shutter components to ensure that the introducer is leak proof, particularly during endovascular surgery.

Conventional apparatuses include deformable valves for surgical instruments in an effort to improve leak proof qualities. However, conventional apparatuses are not fully satisfactory because, when introducing several surgical instruments such as catheters and guides, there remains a gap between the instruments despite the valve, causing a leakage of blood.

WO 2000/032263 discloses an introducer device for use in the human body that includes a main elongated body fitted, at the proximal end, with several openings for surgical instruments. The device has leakage problems because the main elongated body is introduced directly into the human body and the instruments pass there through. Moreover, such conventional system is not easy to use because, once the device has been introduced, there is no way to change the diameter or number of openings in the proximal extremity without withdrawing the device, which results in fluid leakage.

Therefore, a need exists for a device that allows for the simultaneous use of several surgical instruments or instruments of very different sizes via an introducer in the human or animal body that produces a good seal and is easy to use.

SUMMARY OF THE INVENTION

Accordingly, the present disclosure addresses the above problems and disadvantages, and provides an apparatus and a method performing vascular surgery.

An aspect of the present disclosure provides a guiding apparatus that includes an adaptor and an introducer. The adaptor includes a longitudinal section, an elongated body with an outer wall and an inner volume that encloses a plurality of ducts, a proximal section with at least two openings in a proximal end of the proximal section as respective first ends of a plurality of ducts. The introducer accepts the longitudinal section of the adaptor therein, and each duct of the plurality of ducts is configured to pass an instrument from the proximal end of the proximal section to a distal end of the elongated body. In the elongated body, each duct of the plurality of ducts runs in a substantially longitudinal direction within the inner volume. In the proximal section, each duct of the plurality of ducts diverges from the inner volume towards an outer perimeter of the adaptor. The elongated body is provided along an extension of the plurality of ducts from a proximal end of the longitudinal section to the distal end on an opposite end of the elongated body. The introducer includes a proximal portion, a distal portion, and a valve with an inner wall positioned between the proximal portion and the distal portion, and configured to deform by twisting. When the adaptor is fully inserted into the introducer and the valve is not in a deformed state, the inner wall of the valve presses against the outer wall along a part of the elongated body of the adaptor.

Another aspect of the present disclosure provides an apparatus that includes an adaptor and an introducer. The adaptor includes a longitudinal section, an elongated body including an outer wall and an inner volume configured to enclose a plurality of ducts, a proximal section including at least two openings in a proximal end of the proximal section as respective first ends of a plurality of ducts. The introducer is configured to accept the longitudinal section of the adaptor therein. Each duct of the plurality of ducts is configured to pass an instrument from the proximal end of the proximal section to a distal end of the elongated body. In the elongated body, each duct of the plurality of ducts runs in a substantially longitudinal direction within the inner volume. In the proximal section, each duct of the plurality of ducts diverges from the inner volume towards an outer perimeter of the adaptor. The elongated body is provided along an extension of the plurality of ducts from a proximal end of the longitudinal section to the distal end on an opposite end of the elongated body. The introducer includes a proximal portion, a distal portion, and a valve with an inner wall positioned between the proximal portion and the distal portion, and configured to deform by twisting. When the adaptor is fully inserted into the introducer, operating the valve releases the adaptor from the introducer.

A further aspect of the present disclosure provides a method of operation of a guiding apparatus that includes an adaptor and an introducer, by inserting a longitudinal section of the adaptor into the introducer and operating a valve of the introducer by moving a cursor provided on a side wall of the introducer within a travel region of the cursor. Operating the valve either releases the longitudinal section of the adaptor that is being held within the introducer or affixes longitudinal section of the adaptor within the introducer.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE INVENTION

The following detailed description of certain embodiments of the present invention will be made with reference to the accompanying drawings. In describing the invention, explanation about related functions or constructions known in the art are omitted for the sake of clearness in understanding the concept of the invention, to avoid obscuring the invention with unnecessary detail.

Provided is an adaptor configured to affix to an introducer by cooperation with a valve of the introducer. The valve may be formed of a soft, flexible portion in a substantially cylindrical shape with a hollow section of flexible leak proof material, e.g. silicone. When there is no stress on the flexible portion, i.e., the valve is not in a deformed state, a center of the valve closes to maintain an adaptor that is inserted therein. Alternatively, the valve may be configured to maintain the adaptor in the introducer when the valve is in the deformed state.

Figure 1:
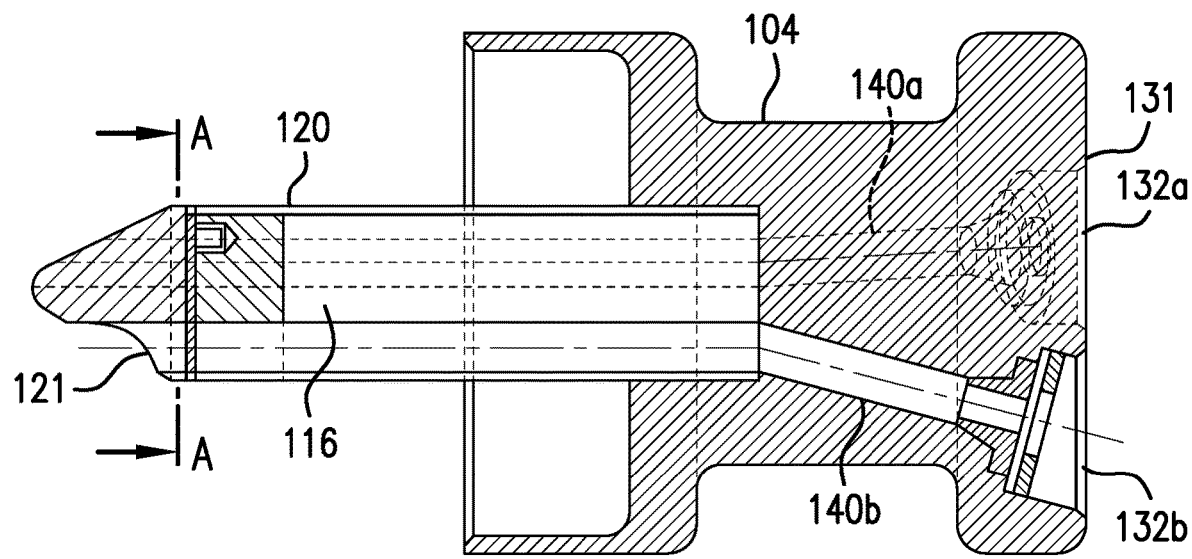
FIG. 1 is a longitudinal cross-section view of an adaptor.
Figure 2:
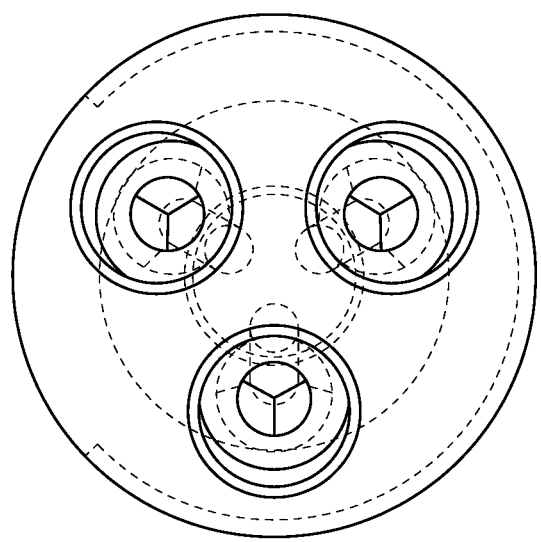
FIG. 2 is a cross-section view from a proximal end of a proximal section of the adaptor of FIG. 1.
Figure 3:
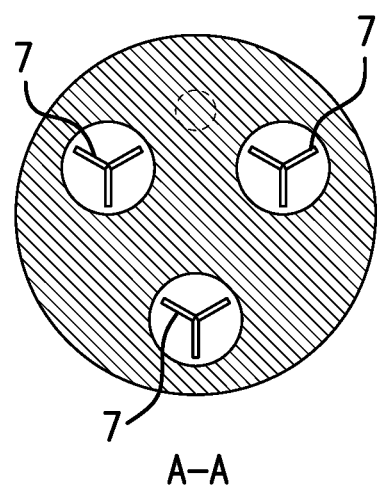
FIG. 3 is a cross-section view of an elongated body of FIG. 1.
Figure 4:
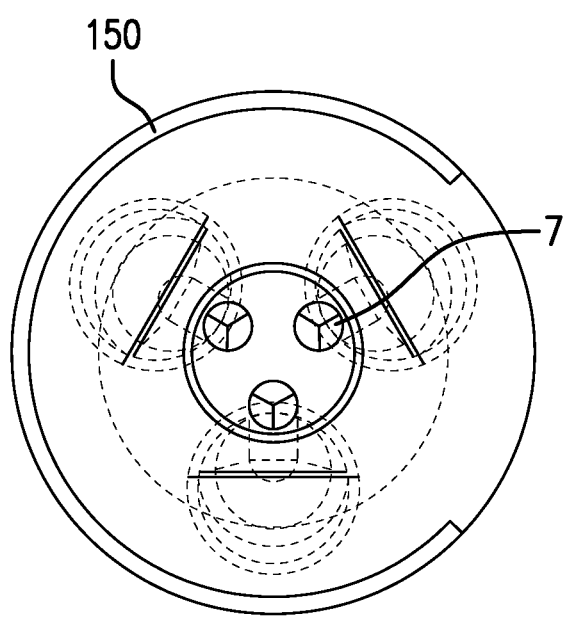
FIG. 4 is a cross-section view from a distal end of the embodiment of the adaptor.

FIG. 1 is a longitudinal cross-section view of an adaptor, FIG. 2 is a cross-section view from a proximal end of a proximal section of the adaptor of FIG. 1, FIG. 3 is a cross-section view of an elongated body of FIG. 1, and FIG. 4 is a cross-section view from a distal end of the embodiment of the adaptor.

Stress is applied to the valve by a user, e.g. a surgeon, rotating an extremity, such as by moving a cursor affixed to a cable that attaches to an opposite end of the valve. Twisting the flexible portion may open an area approximately in the middle the valve, thereby increasing the size of the opening of the valve that is provided within the introducer.

Accordingly, when an object such as the adaptor is to be introduced into the introducer, the operator may operate the cursor to open the valve.

FIGS. 1-4 illustrate an adaptor, which may include a plurality, e.g., three, ducts each with at least one leak proof valve at proximal and/or distal end thereof. Each duct of the plurality of ducts (140) may include a haemostatic valve (7) at a distal end thereof. The tricuspid valve may be formed of a flexible silicon or with polymer washer in a center of thereof, with three slots that enable leak-proof passage of surgical and/or medical instruments. The haemostatic valve may be held in place between a valve support and a washer, which are pierced with a passage of a same diameter as the respective duct of the plurality of ducts, to enable the introduction of surgical instruments of varied size. The ducts may include a removable stopper at a proximal end thereof to close off unused ducts by placing the stopper above the haemostatic valve and washer. The ducts may include centers with proximal openings arranged in a predetermined circle, with a channel provided in a center of the circle.

Figure 5:
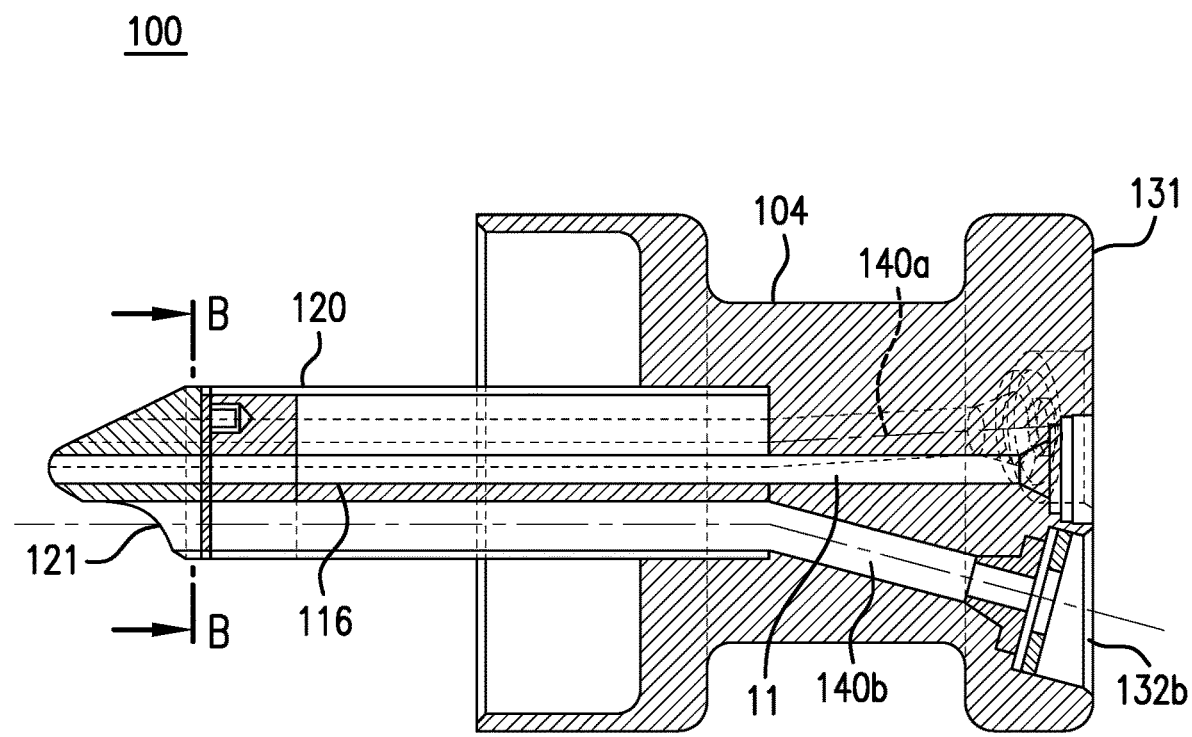
FIG. 5 is a longitudinal cross-section illustrating a central channel.
Figure 6:
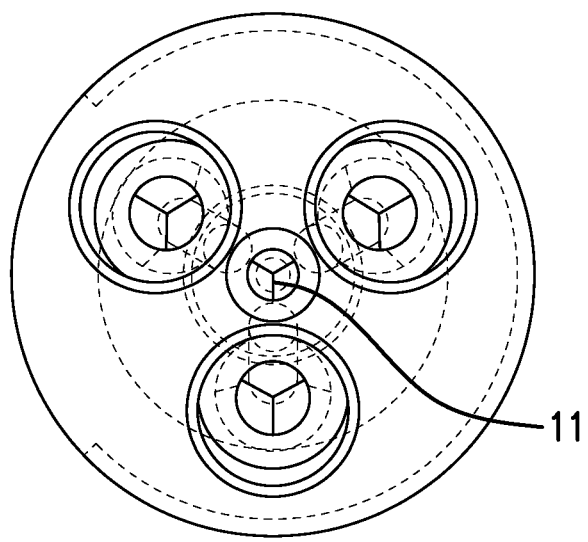
FIG. 6 is a cross-section from a proximal end of a proximal section of the adaptor of FIG. 5.
Figure 7:
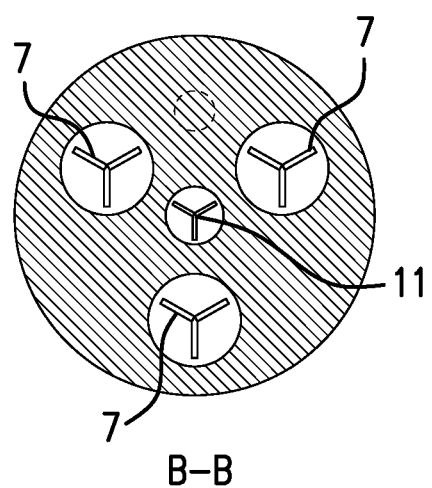
FIG. 7 is a cross-section view of an elongated body of FIG. 5.
Figure 8:
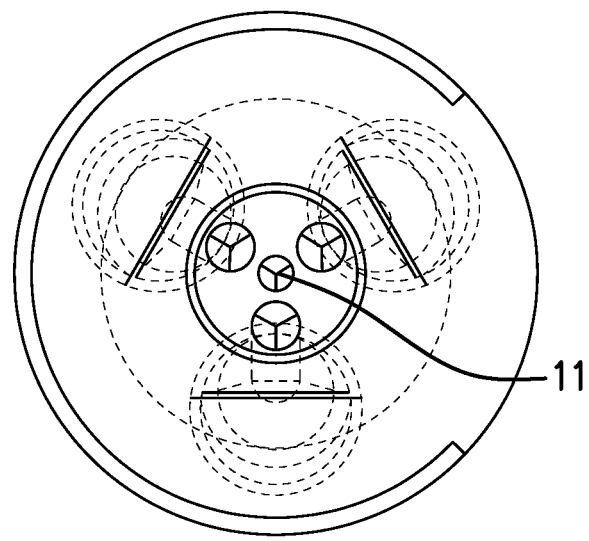
FIG. 8 is a cross-section view from a distal end of the embodiment of the adaptor.

FIG. 5 is a longitudinal cross-section illustrating a central channel, FIG. 6 is a cross-section from a proximal end of a proximal section of the adaptor of FIG. 5, FIG. 7 is a cross-section view of an elongated body of FIG. 5, and FIG. 8 is a cross-section view from a distal end of the embodiment of the adaptor.

The central channel (11) may include one or more leak-proof valves and may be rectilinear to simplify handling of surgical/medical instruments and allow passage of a guide wire. The plurality of ducts may be provided with a first section in which the ducts outwardly diverge in a proximal section (130) of the adaptor (100), and a second section in which a continuation of the ducts are longitudinally configured in an elongated body (120) of the adaptor, to facilitate ease of introduction of surgical/medical instruments by the user during surgery or other medical procedures.

Figure 9:
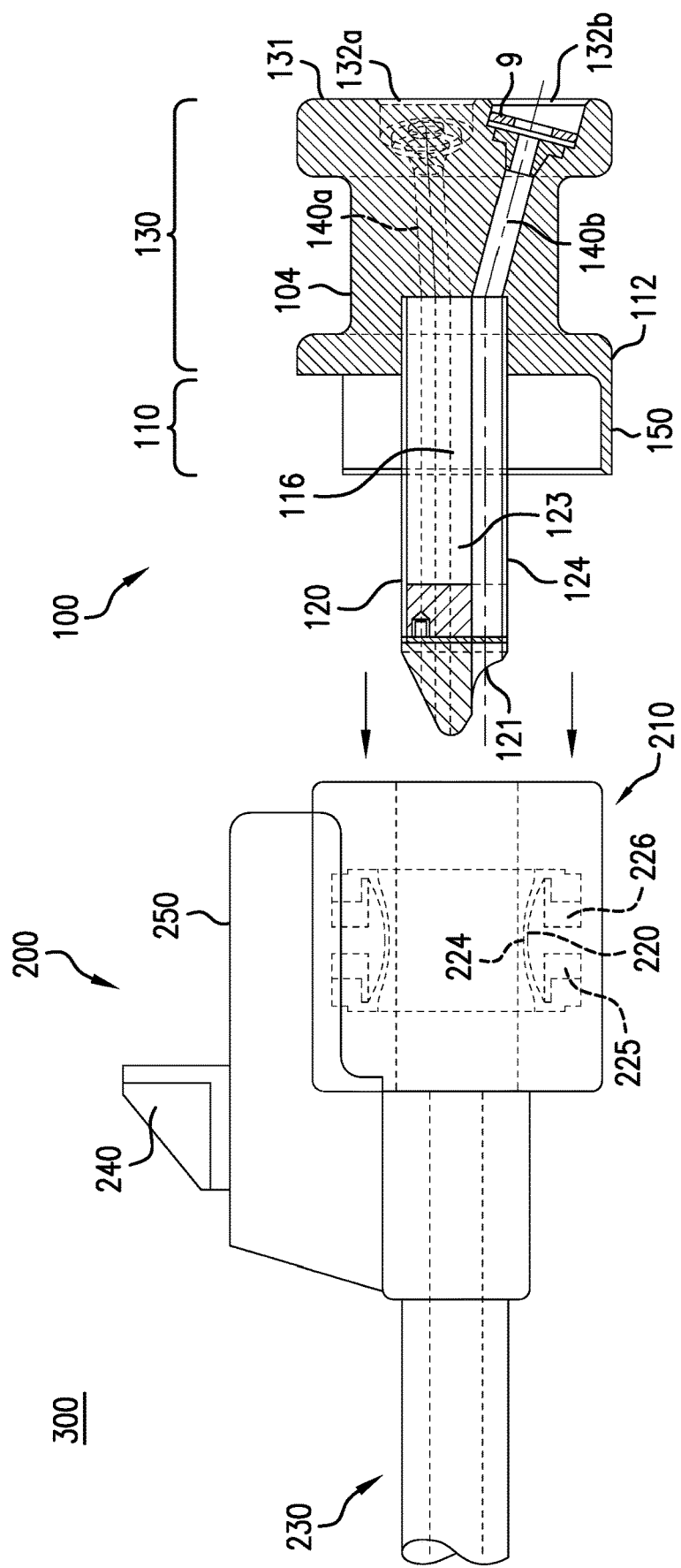
FIG. 9 is a longitudinal view of the adaptor before joining with an introducer.
Figure 10:
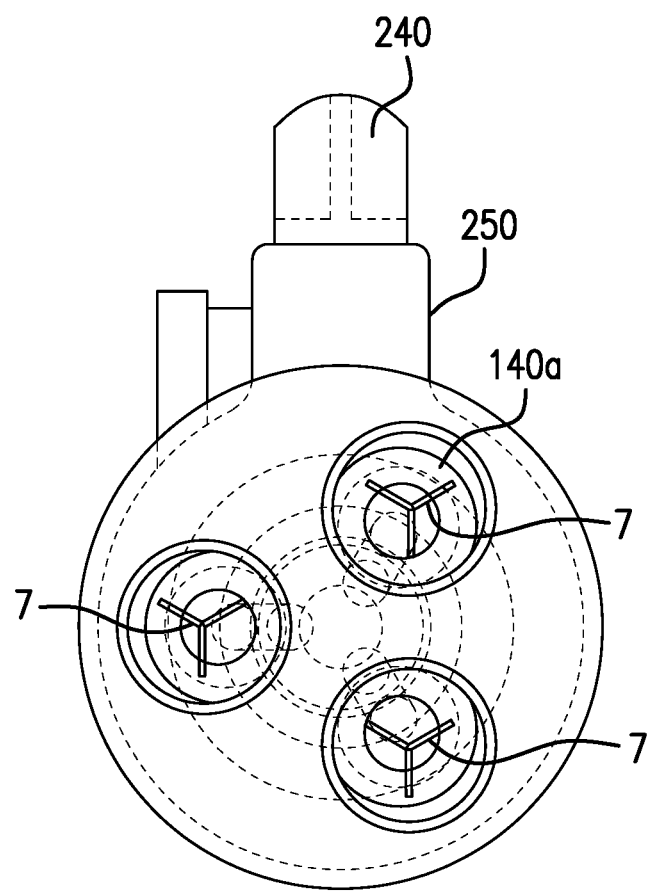
FIG. 10 is a cross-sectional view of the adaptor according to FIG. 9.
Figure 11:
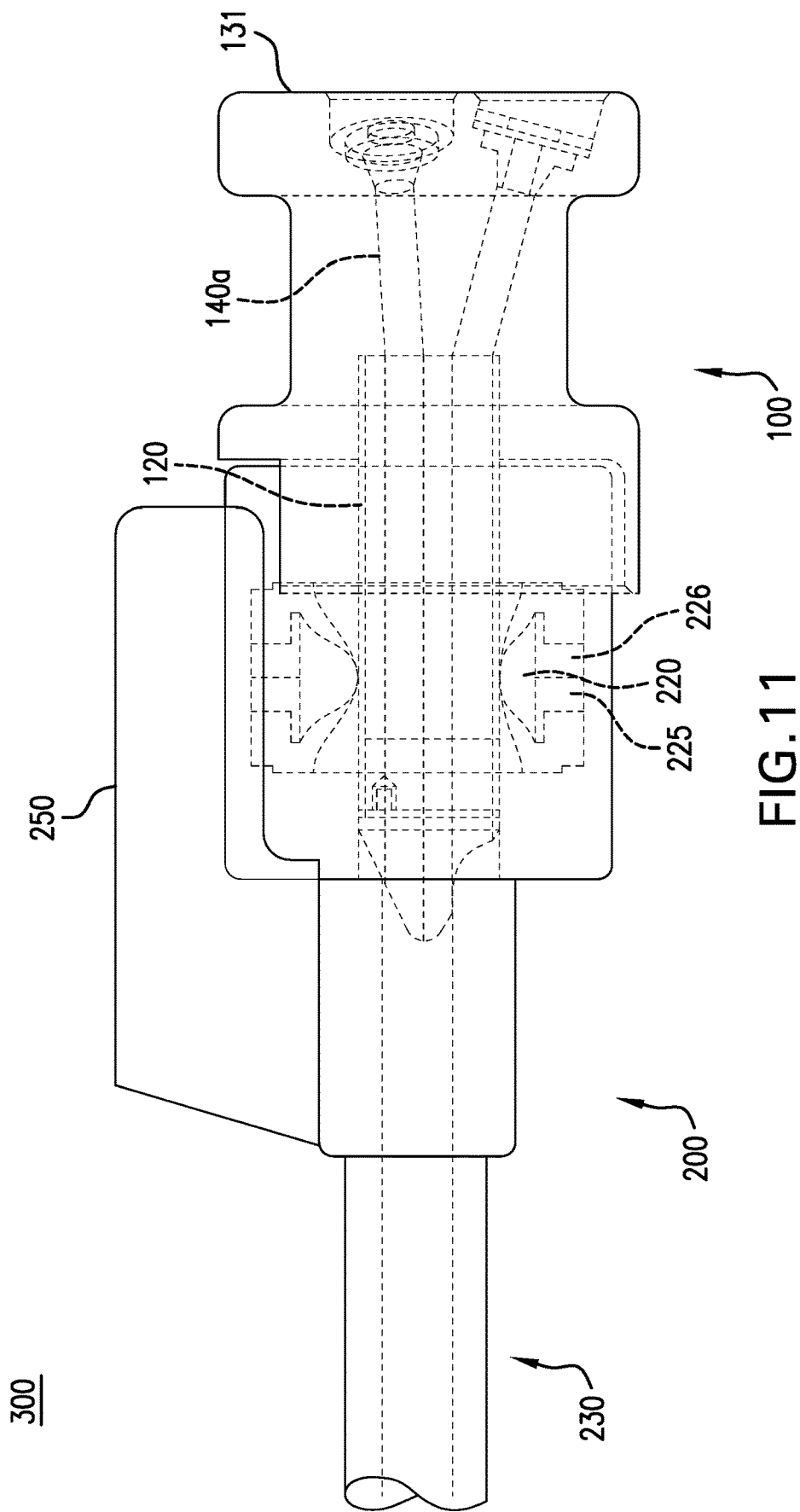
FIG. 11 is a longitudinal sectional view of the adaptor mounted on the introducer.

FIG. 9 is a longitudinal view of the adaptor before joining with an introducer, FIG. 10 is a cross-sectional view of the adaptor according to FIG. 9; and FIG. 11 is a longitudinal sectional view of the adaptor mounted on the introducer.

As shown in FIGS. 9-11, a guiding apparatus (300) is provided that includes the adaptor (100) and the introducer (200), for vascular surgery. The introducer (200) and the adaptor (100) are configured as two distinct pieces, and the adaptor (100) is configured to be inserted into or withdrawn from the introducer (200).

The adaptor (100) includes a longitudinal section (110), an elongated body (120), and a proximal section (130). The elongated body (120) includes an outer wall (124) and an inner volume (123), which encloses a plurality of ducts (140). The proximal section (130) includes at least two openings (132*a*, 132*b*) in a proximal end (131) of the proximal section (130) as respective first ends of a plurality of ducts.

The introducer (200) is configured to accept the longitudinal section (110) of the adaptor (100) therein. Each duct of the plurality of ducts (400) is configured to facilitate at least one instrument passing from the proximal end (131) of the proximal section (130) to a distal end (121) of the elongated body (120).

When in the elongated body (120), each duct of the plurality of ducts runs in a substantially longitudinal direction near or within the inner volume (123). When in the proximal section (130), each duct of the plurality of ducts diverges from the inner volume (123) towards an outer perimeter (104) of the adaptor (101). Accordingly, the elongated body (120) is provided along an extension of the plurality of ducts (140) from a proximal end (112) of the longitudinal section (110) to the distal end (121) on an opposite end of the elongated body (120), and the longitudinal section (110) includes a longitudinal axis (116).

The introducer (200) includes a proximal portion (210), a distal portion (230), and a valve (220). The valve (220) includes an inner wall (224) positioned between the proximal portion (210) and the distal portion (230). The valve (220) deforms by twisting.

When the adaptor (100) is fully inserted into the introducer (200) and the valve (220) is not in the deformed state, the inner wall (224) of the valve (220) presses against the outer wall (124) along a part of the elongated body (120) of the adaptor (100).

Each duct of the plurality of ducts (400) may have a different diameter from each other duct of the plurality of ducts (400), and the instrument that passes through each duct of the plurality of ducts (400) may be a surgical instrument or a medical instrument.

The elongated body may be substantially cylindrically shaped and extend along the longitudinal axis (116) from the proximal end (112) of the longitudinal section (110) away from the proximal section (130). A first opening (132*a*) of the proximal section (130) is spaced apart from a second opening (132*b*) along a spacing direction perpendicular to the longitudinal axis (116).

The adaptor (100) may also include a skirt (150) that is spaced apart from the elongated body (120) away from the longitudinal axis (116). The skirt (150) extends along the longitudinal axis (116) and is spaced apart from the elongated body (120), including an inner surface (152) that partially surrounds the outer wall (124) of the elongated body (120). The skirt (150) may partially surround the outer wall (124) along an angular sector of less than 360°.

Twisting the valve (220) of the introducer (200) may release the inner wall (224) of the valve (220) from pressing against the outer wall (124) of the elongated body (120) of the adaptor (100), to detach the adaptor (100) from being fixedly held within the introducer (200).

As shown in FIG. 9, a conical end is provided on an extremity of the elongated body (120) to facilitate opening valve (220) for insertion of adaptor (100) in the introducer (200), by the conical end exerting pressure on valve (220) as the user moves the adaptor (100) in the longitudinal direction toward the introducer (200), to gradually open the valve (220), with the valve (220) continuing to press against the elongated body (120) of the adaptor (100), thereby avoiding leakage.

The introducer (200) may also include a cursor (240) positioned on a side wall of the introducer (200). Operation of the cursor (240) within a travel region of the cursor (240) causes an extremity (225) of the valve (220) to rotate, relative to an opposite end (226) of the valve (220). Operation of the cursor (240) in the travel region moves the cursor (240) in a direction parallel to a longitudinal axis (116). The travel region of the cursor (240) is distinct from the side wall (250) of the introducer (200).

Also provided is a method of operation of the apparatus (300) by inserting a longitudinal section (110) of the adaptor (100) into the introducer (200) and operating a valve (220) of the introducer (200) by moving a cursor (240) provided on a side wall of the introducer (200) within a travel region of the cursor (240). Operating the valve (220) fixedly attaches the longitudinal section (110) of the adaptor (100) within the introducer (200), and moving the cursor (240) rotates an extremity (225) of the valve (220) relative to an opposite end (226) of the valve (220).

While the invention has been shown and described with reference to certain aspects thereof, it will be understood by those skilled in the art that various changes in form and details may be made therein without departing from the spirit and scope of the present invention as defined by the appended claims and equivalents thereof.

What is claimed is:

1. A guiding apparatus, comprising:
    an adaptor; and
    an introducer,
    wherein the adaptor comprises:
        a longitudinal section,
        an elongated body comprising an outer wall and an inner volume configured to enclose a plurality of ducts,
        a proximal section comprising at least two openings in a proximal end of the proximal section as respective first ends of the plurality of ducts,
        wherein the introducer is configured to accept the longitudinal section of the adaptor therein,
        wherein each duct of the plurality of ducts is configured to pass an instrument from the proximal end of the proximal section to a distal end of the elongated body,
        wherein, in the elongated body, each duct of the plurality of ducts runs in a substantially longitudinal direction within the inner volume,
        wherein, in the proximal section, each duct of the plurality of ducts diverges from the inner volume towards an outer perimeter of the adaptor,
        wherein the elongated body is provided along an extension of the plurality of ducts from a proximal end of the longitudinal section to the distal end on an opposite end of the elongated body,
    wherein the introducer comprises:
        a proximal portion,
        a distal portion, and
        a valve comprising an inner wall positioned between the proximal portion and the distal portion, and configured to deform by twisting,
    wherein, when the adaptor is fully inserted into the introducer and the valve is not in a deformed state, the inner wall of the valve presses against the outer wall along a part of the elongated body of the adaptor,
    wherein the adaptor further comprises a skirt spaced apart from the elongated body away from the longitudinal axis, and
    wherein the skirt extends along the longitudinal axis and includes an inner surface that partially surrounds the outer wall of the elongated body.

2. The apparatus of claim 1, wherein the each duct of the plurality of ducts has a different diameter from each other duct of the plurality of ducts.

3. The apparatus of claim 1, wherein the instrument that passes through each duct of the plurality of ducts is at least one of a surgical instrument and a medical instrument.

4. The apparatus of claim 1, wherein the longitudinal section includes a longitudinal axis.

5. The apparatus of claim 4, wherein the elongated body is substantially cylindrically shaped and extends along the longitudinal axis from the proximal end of the longitudinal section away from the proximal section of the adaptor.

6. The apparatus of claim 4, wherein a first opening of the proximal section is spaced apart from a second opening along a spacing direction perpendicular to the longitudinal axis.

7. The apparatus of claim 1, wherein the skirt partially surrounds the outer wall along an angular sector of less than 360°.

8. The apparatus of claim 1, wherein twisting the valve of the introducer releases the inner wall of the valve from being held against the outer wall of the elongated body of the adaptor, to release the adaptor from being fixedly held within the introducer.

9. The apparatus of claim 1, wherein the introducer further comprises a cursor positioned on a side wall of the introducer.

10. The apparatus of claim 9, wherein operation of the cursor within a travel region of the cursor causes an extremity of the valve to rotate, relative to an opposite end of the valve.

11. A guiding apparatus, comprising:
    an adaptor; and
    an introducer,
    wherein the adaptor comprises:
        a longitudinal section,
        an elongated body comprising an outer wall and an inner volume configured to enclose a plurality of ducts, a proximal section comprising at least two openings in a proximal end of the proximal section as respective first ends of the plurality of ducts, wherein the introducer is configured to accept the longitudinal section of the adaptor therein, wherein each duct of the plurality of ducts is configured to pass an instrument from the proximal end of the proximal section to a distal end of the elongated body, wherein, in the elongated body, each duct of the plurality of ducts runs in a substantially longitudinal direction within the inner volume, wherein, in the proximal section, each duct of the plurality of ducts diverges from the inner volume towards an outer perimeter of the adaptor, wherein the elongated body is provided along an extension of the plurality of ducts from a proximal end of the longitudinal section to the distal end on an opposite end of the elongated body, wherein the introducer comprises:

a proximal portion, a distal portion, and a valve comprising an inner wall positioned between the proximal portion and the distal portion, and configured to deform by twisting, wherein, when the adaptor is fully inserted into the introducer and the valve is not in a deformed state, the inner wall of the valve presses against the outer wall along a part of the elongated body of the adaptor, wherein the introducer further comprises a cursor positioned on a side wall of the introducer, wherein operation of the cursor within a travel region of the cursor causes an extremity of the valve to rotate, relative to an opposite end of the valve, and wherein operation of the cursor in the travel region moves the cursor in a direction parallel to a longitudinal axis, and the travel region of the cursor is distinct from the side wall of the introducer.

12. The apparatus of claim 1, wherein the introducer and the adaptor are configured as two distinct pieces.

13. The apparatus of claim 1, wherein the adaptor is configured to be inserted into or withdrawn from the introducer.

14. The apparatus of claim 1, wherein at least two ducts of the plurality of ducts comprise a haemostatic valve and the apparatus is adapted for vascular surgery.

* * * * *